United States Patent
Krebs et al.

(10) Patent No.: US 7,875,000 B2
(45) Date of Patent: Jan. 25, 2011

(54) DISPOSABLE BREAST CUP SET

(75) Inventors: Yvonne Krebs, Gattikon (CH); Stefan Vögelin, Auw (CH); Urs Stadelmann, Pfeffikon (CH)

(73) Assignee: Medela Holding AG, Baar (CH)

( * ) Notice: Subject to any disclaimer, the term of this patent is extended or adjusted under 35 U.S.C. 154(b) by 611 days.

(21) Appl. No.: 11/578,635

(22) PCT Filed: May 26, 2005

(86) PCT No.: PCT/CH2005/000298

§ 371 (c)(1),
(2), (4) Date: Oct. 17, 2006

(87) PCT Pub. No.: WO2005/118023

PCT Pub. Date: Dec. 15, 2005

(65) Prior Publication Data

US 2007/0173756 A1    Jul. 26, 2007

(30) Foreign Application Priority Data

Jun. 3, 2004 (WO) ............... PCT/CH2004/000334

(51) Int. Cl.
*A61M 1/06* (2006.01)
*A61M 25/00* (2006.01)

(52) U.S. Cl. .................... 604/73; 604/523; 604/74; 604/75

(58) Field of Classification Search ............. 604/73–74; 222/182, 23
See application file for complete search history.

(56) References Cited

U.S. PATENT DOCUMENTS

| | | | | |
|---|---|---|---|---|
| 4,772,262 A | * | 9/1988 | Grant et al. | 604/74 |
| 4,798,301 A | * | 1/1989 | Bullock et al. | 215/256 |
| 5,308,321 A | * | 5/1994 | Castro | 600/415 |
| 5,775,528 A | * | 7/1998 | Wohlgemuth et al. | 215/256 |
| 5,941,847 A | * | 8/1999 | Huber et al. | 604/74 |
| 6,110,140 A | | 8/2000 | Silver | |
| 6,112,923 A | * | 9/2000 | Ma | 215/252 |
| 6,383,163 B1 | * | 5/2002 | Kelly et al. | 604/74 |
| 6,461,324 B1 | | 10/2002 | Schlensog | |
| 6,749,582 B2 | * | 6/2004 | Britto et al. | 604/74 |
| 6,884,229 B2 | * | 4/2005 | Renz | 604/74 |
| 6,974,439 B1 | * | 12/2005 | McKendry | 604/74 |

(Continued)

FOREIGN PATENT DOCUMENTS

| | | |
|---|---|---|
| GB | 550 187 A | 12/1942 |
| JP | 01-240455 | 9/1989 |
| JP | 2002-302133 | 10/2002 |

*Primary Examiner*—Nicholas D Lucchesi
*Assistant Examiner*—Ian K Holloway
(74) *Attorney, Agent, or Firm*—McDonnell Boehnen Hulbert & Berghoff LLP

(57) ABSTRACT

The invention relates to a disposable breast cup set which comprises a coupling element (2) to be coupled to a milk collection receptacle (1) and a breast cup connecting element (3) to be coupled to a breast cup funnel (5). The coupling element (5) and the breast cup connecting element (3) are interlinked via a tamper-evident element (4), said connection being destroyed when the coupling element (2) is for the first time separated from the breast cup connecting element (3) and preventing re-use of the set.

17 Claims, 11 Drawing Sheets

U.S. PATENT DOCUMENTS

| | | |
|---|---|---|
| 7,166,087 B2 * | 1/2007 | Silver et al. .................. 604/74 |
| 7,445,130 B2 * | 11/2008 | Bosl et al. .................. 215/252 |
| 2003/0230351 A1 | 12/2003 | Renz |
| 2004/0087898 A1 * | 5/2004 | Weniger .................. 604/74 |
| 2005/0154349 A1 * | 7/2005 | Renz et al. .................. 604/74 |
| 2006/0148380 A1 * | 7/2006 | Rousso et al. .................. 450/36 |

* cited by examiner

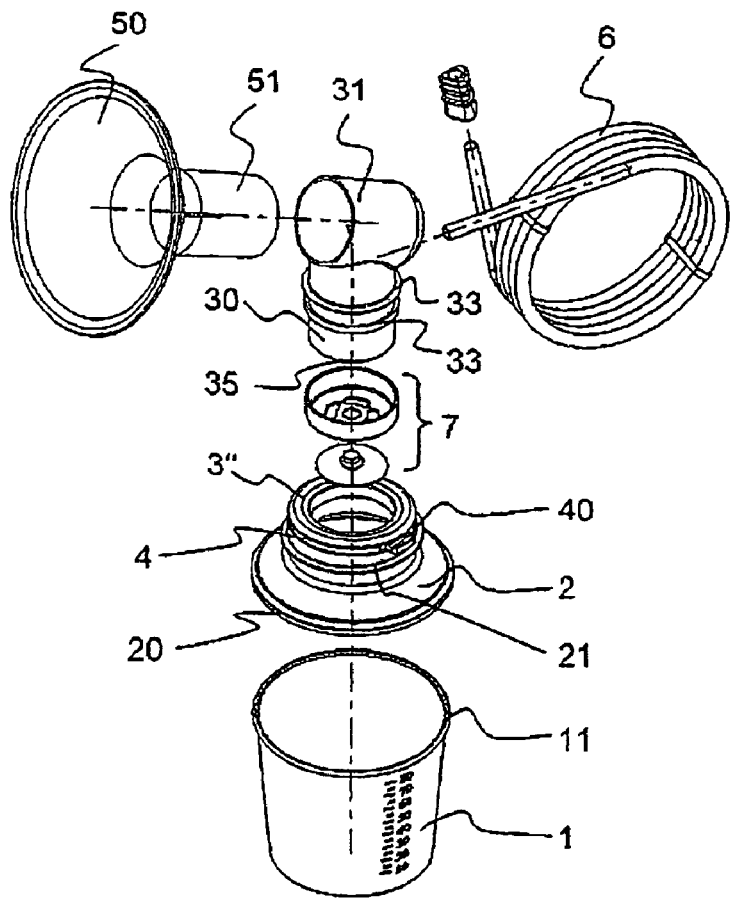
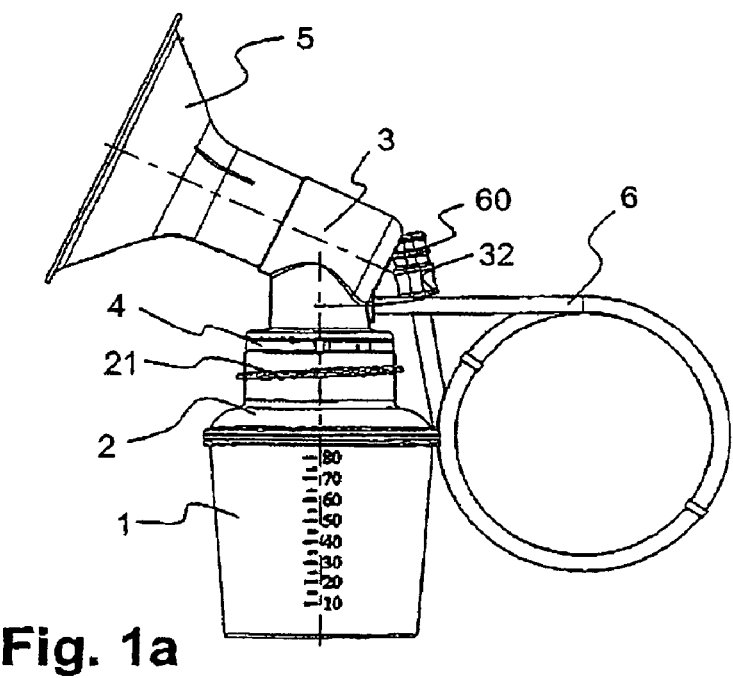
Fig. 1b
Fig. 1a

Fig. 1c
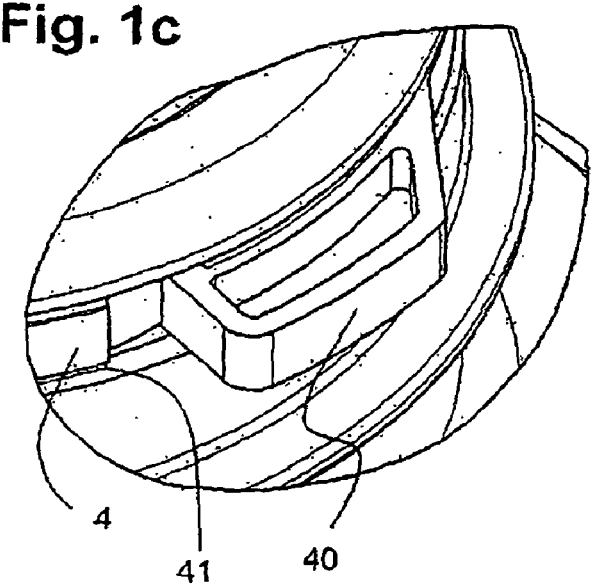
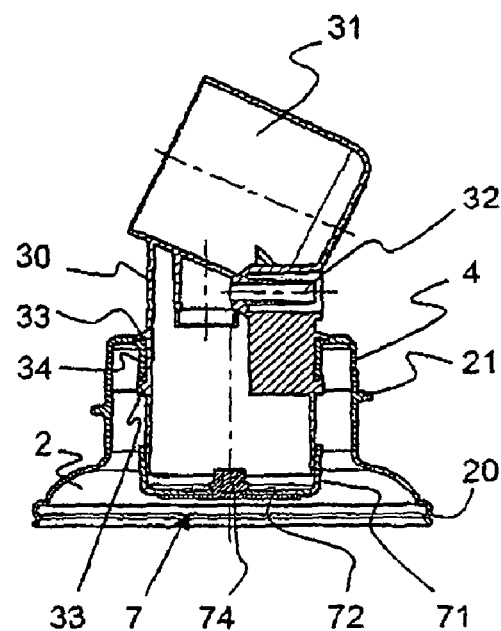
Fig. 1d
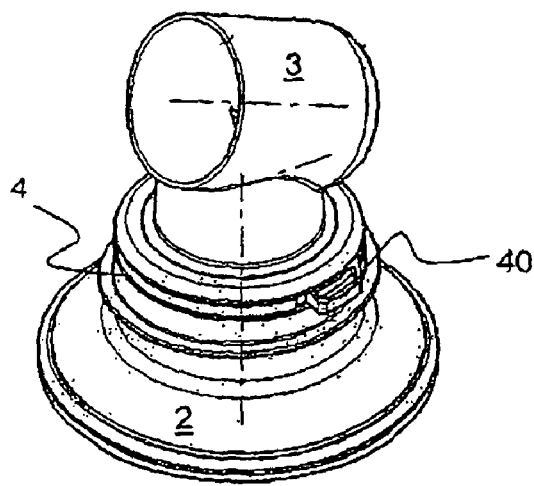
Fig. 1e

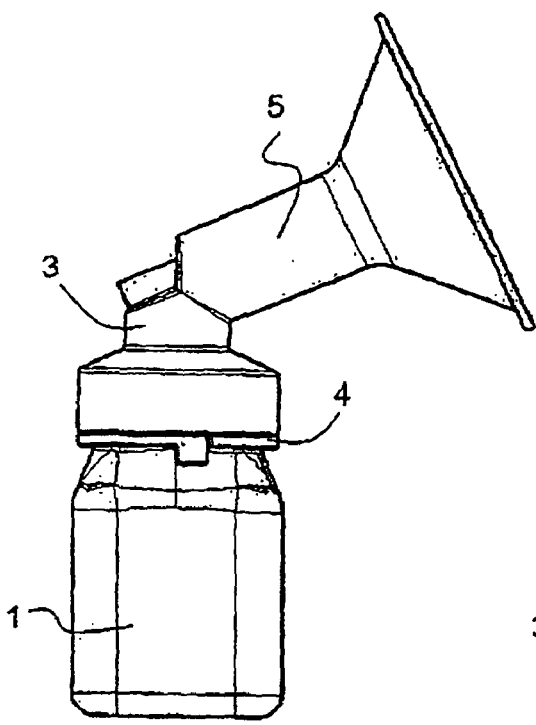
Fig. 3a
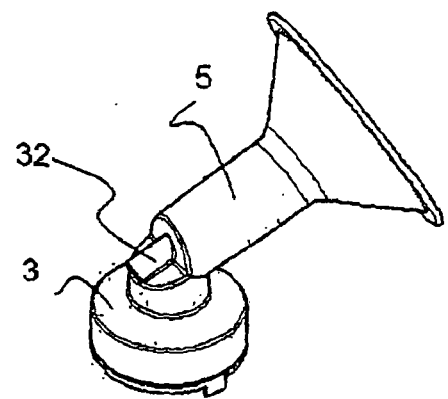
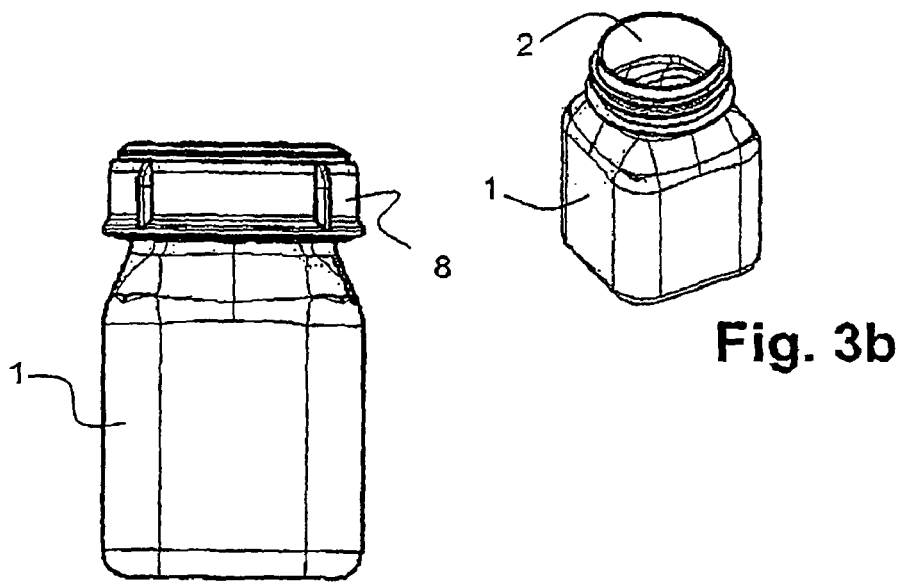
Fig. 3b
Fig. 3c

DISPOSABLE BREAST CUP SET

FIELD OF THE INVENTION

This invention relates to a disposable breast cup set.

PRIOR ART

Breast cup sets of this kind are used together with breast pumps to pump off human breast milk. They normally comprise a breast cup funnel which is connected via a breast cup attachment part to a coupling part. The coupling part can be screwed onto a milk collection receptacle, preferably a baby's milk bottle made of glass or plastic. The breast cup attachment part can either be connected to a mechanical pump mechanism or it has a connector piece for a connection tube that can be attached to an electrical breast pump. A breast cup set of this kind is described in U.S. Pat. No. 6,461,324, for example.

These breast cup sets are usually made of plastic. They can often be sterilized and autoclaved and can therefore be used more than once. However, increased hygiene demands, both in hospital use and in domestic use, have in recent years heightened the need for a disposable and therefore inexpensive breast cup set.

Disposable sets are indeed already known. However, these can nevertheless be used a number of times, which in some cases is also done for reasons of cost. Moreover, U.S. Pat. No. 6,575,202 discloses a breast cup set with a collection receptacle, where the collection receptacle itself can be disposed of, but not the remaining elements.

SUMMARY OF THE INVENTION

It is therefore an object of the invention to make available a breast cup set that satisfies the increased hygiene demands and nevertheless can be produced inexpensively.

The breast cup set according to the invention comprises a coupling part for connection to a milk collection receptacle, and a breast cup attachment part for connection to a breast cup funnel, the coupling part and the breast cup attachment part being connected to one another via an irreversibly destructible connection in the form of a tamper-evident element. The tamper-evident element is designed in such a way that the connection between the breast cup attachment part and the coupling part is basically destroyed irreversibly the first time the coupling part and the breast cup attachment part are separated or the first time the tamper-evident element is removed. This can be done, for example, by the tamper-evident element being removed, detached, torn open, pulled off or the like.

The first time they have been separated, the coupling part and the breast cup attachment part cannot be connected to one another again or, if they can, at least not very well. Since separation for the first time is necessary in order to store the milk or administer the milk, both parts can be used just one time for pumping off milk.

The expression tamper-evident element is therefore to be understood in the present case as an element which is in intact form on the unused device, that is to say on the unused breast cup set, and which is also normally left in this state while the breast milk is being pumped off.

However, at the time when the user has finished pumping off the milk, or the collection receptacle is full, and wishes to use or store the breast milk collected in the collection receptacle, it is necessary to manipulate this tamper-evident element in order to remove the upper part of the breast cup set. To achieve the possibility of removing the upper part, that is to say the breast cup attachment part, the tamper-evident element has to be manipulated in a way that irreversibly breaks or tears open the connection, so that it is basically destroyed.

For this purpose, the tamper-evident element has a predetermined break point, for example, which is broken or torn open in order to separate the parts from one another. The connection between the breast cup attachment part and the coupling part is also preferably designed such that, after the tamper-evident element has been broken open, these two parts cannot any longer be readily connected to one another.

It must be emphasized that the tamper-evident element is not to be understood as meaning some kind of element that can be destroyed by application of force. The tamper-evident element, as it is understood here, is an element that is irreversibly destroyed when the breast cup set is handled in the intended manner, i.e. in which the irreversible destruction of the element, in addition to having a connection function between breast cup attachment part and coupling part, is the actual objective and occurs when the set is handled in the manner intended.

In construction terms, this is reflected by the fact that, without irreversible destruction of the tamper-evident element, it is not at all possible to separate the breast cup attachment part and coupling part from one another and, for example, to remove the contents of the collection vessel or to store them without a cover. The coupling part and breast cup attachment part can therefore only be separated from one another in the intended manner when the tamper-evident element has first been irreversibly destroyed. It is also possible for several tamper-evident elements to be provided.

Therefore, the tamper-evident element within the meaning of the invention is not an element which is provided per se for such a tamper-proofing function and which can only be irreversibly destroyed by inappropriate forceful manipulation.

This tamper-evident element is comparable, for example, to a seal and, accordingly, it can take the form of a paper strip, plastic strip or corresponding bands that are provided at a dividing line between the breast cup attachment part and the coupling part. The tamper-evident element can thus, for example, be adhesively bonded as a paper strip onto the breast cup attachment part and the coupling part.

In the simplest embodiment, the breast cup set according to the invention comprises, within the meaning of the invention, the coupling part, the breast cup attachment part and the tamper-evident element, said coupling part and breast cup attachment part being able to be connected to the breast cup funnel or to the milk collection receptacle, respectively, in a releasable or nonreleasable manner or are already connected to them. Depending on the embodiment, the breast cup set can have additional elements. For example, the coupling part and breast cup attachment part can be formed integrally with other parts, in particular the collection receptacle and the breast cup. If the coupling part is connected to or integrally formed on a milk collection receptacle in a manner that does not allow it to be released without being destroyed, this also ensures that the milk collection receptacle is only then used for storing or for administering the milk and cannot be used again for collecting new milk.

The coupling part is preferably designed as a separate part and is only connected to the collection receptacle shortly before use. In this way, the collection receptacle can be made in the form of a beaker and can thus be stacked. This embodiment has the advantage that the space required for transport and storage of the breast cup set is less than in a one-piece set or a ready-assembled set.

The breast cup funnel, with the funnel element applied to the breast, can preferably be connected to the breast cup attachment part in a releasable manner. The breast cup funnel can preferably be plugged into the breast cup attachment part. This also has the advantage of reducing the space required for transport and storage. Moreover, depending on the shape and size of the breast, different breast cup funnel shapes and sizes can be used, without the rest of the set having to be adapted. This reduces the production costs and once again saves on space.

In preferred embodiments, the breast cup set is provided with a disposable valve that reduces the dead volume in the set and thus increases the efficiency of the suction process.

Further advantageous embodiments are set out in the dependent patent claims.

BRIEF DESCRIPTION OF THE DRAWINGS

The subject matter of the invention is explained in more detail below on the basis of preferred illustrative embodiments shown in the attached drawings, in which:

FIG. 1a shows a side view of a breast cup set according to the invention in a first embodiment;

FIG. 1b shows the breast cup set according to FIG. 1a in an exploded view;

FIG. 1c shows an enlarged representation of a part of FIG. 1b;

FIG. 1d shows a longitudinal section through an upper part of the breast cup set according to FIG. 1a;

FIG. 1e shows a perspective representation of the upper part according to FIG. 1d;

FIG. 1k shows an enlarged representation of the disposable valve according to FIG. 1a;

FIG. 3a shows a side view of a breast cup set according to the invention in a third embodiment;

FIG. 3b shows a breast cup set according to FIG. 3a in an exploded view;

FIG. 3c shows the milk collection receptacle according to FIG. 3a with a closure lid;

FIG. 5b shows a longitudinal section through the part according to FIG. 5a;

FIG. 7c shows a longitudinal section through the valve according to FIG. 7a;

FIG. 8b shows a view of the valve according to FIG. 8a;

FIG. 9c shows a longitudinal section through the valve according to FIG. 9a.

DETAILED DESCRIPTION OF THE EMBODIMENTS OF THE INVENTION

Figure 1F:
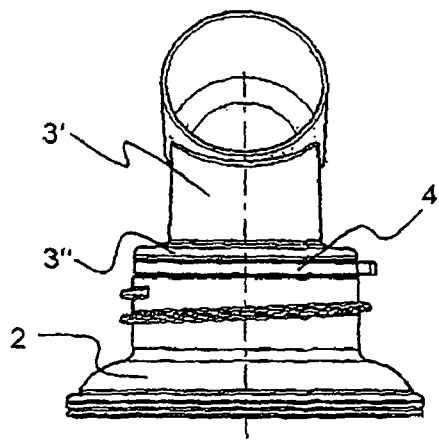
FIG. 1f shows a view of the upper part according to FIG. 1e, from a first side.

A first illustrative embodiment of the disposable breast cup set according to the invention is shown in FIGS. 1a to 1k. The individual parts are preferably made of plastic.

As is shown in FIG. 1a, a milk collection receptacle 1 is connected to a breast cup attachment part 3 via a coupling part 2. A breast cap funnel 5 is held in the breast cup attachment part 3 and is applied to a mother's breast when breast milk is being pumped off. The breast cup attachment part 3 has a pump-side connector piece 32 to which a first end of a connection tube 6 can be attached. A second end 60 of the connection tube 6 can be connected to an electrical or mechanical breast pump (not shown here) or to a central vacuum (that is to say a ready-to-use suction unit). The breast pump generates an underpressure in a cyclical rhythm in the breast cup, such that the breast is stimulated and milk can pass through the breast cup attachment part 3 into the collection receptacle 1.

As can be seen from FIG. 1b, a nonreturn valve 7 is preferably present in the area between breast cup attachment part 3 and collection receptacle 1. This valve 7 closes the receptacle-side inlet opening 35 of the breast cap attachment part 3 and thus reduces to a minimum the dead volume that has to be evacuated by means of the pump.

According to the invention, a tamper-evident element 4 is provided which connects the breast cup attachment part 3 and the coupling part 2 to one another. A suitable tamper-evident element takes the form of any type of connection that irreversibly destroys the connection between the breast cup attachment part 3 and the coupling part 2 the first time these two parts are separated or the first time it is removed.

This tamper-evident element 4 is preferably a tear-open seal, for example a circumferential band which is connected to the coupling part 2 and to the breast cup attachment part 3 via thin webs 41 that tear at the moment of separation. The tamper-evident element 4 is usually also made of plastic and is injection molded onto one of the two parts or onto both parts 2, 3.

The tamper-evident element 4 preferably has a protruding tab 40 so that it can be easily gripped by hand and can be easily torn open. This is shown in FIG. 1c.

The individual parts of the breast cup set that have been mentioned above can be designed in one or more pieces. Two or more of these parts can also be integrally formed.

As can be seen in FIG. 1b, the first illustrative embodiment consists of several individual parts. The collection receptacle 1 is a cylindrical beaker which, at its upper edge, has a first lower snap-fit closure element 11 in the form of a circumferential bead. At its lower edge, the coupling part 2 has a first upper snap-fit closure element 20 in the form of a circumferential latch. When these two elements are plugged together, the latch engages round the bead and thus forms a secure connection between coupling part 2 and collection receptacle 1.

In this embodiment, the breast cup attachment part 3 is designed in two pieces. It has an upper element 3' with a receptacle-side connector piece 30 and a funnel-side connector piece 31. The breast cup funnel 5 has a funnel element 50 for application to the breast, and a funnel connector 51 which can be fixedly attached or can be plugged into the funnel side connector piece 31 and can also be easily removed again from this.

A lower element 3" of the breast cup attachment part 3 is connected to the coupling part 2 via the tamper-evident element 4.

The valve 7, here consisting of a valve membrane 70 and of a valve body 71, is preferably fitted on the lower edge of the receptacle-side connector piece 30, as can be seen clearly from FIG. 1d.

Figure 1G:
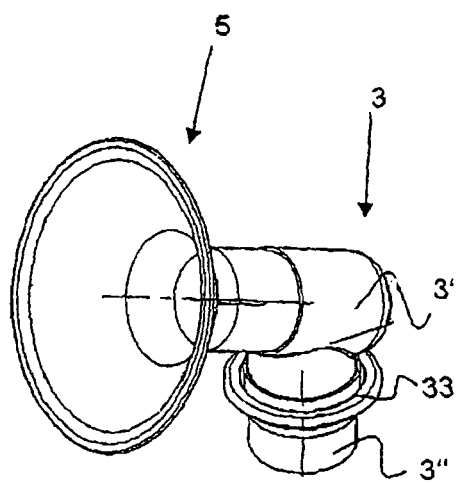
FIG. 1g shows a view of the upper part according to FIG. 1e from a second side.
Figure 1G:
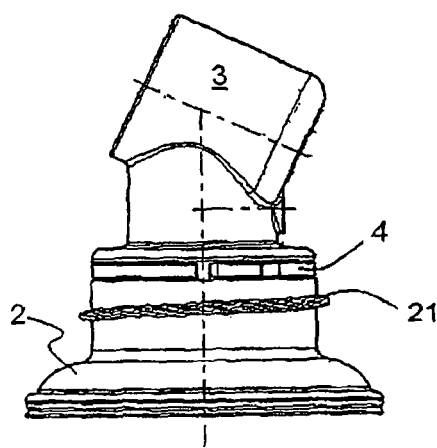

Arranged on the receptacle-side connector piece 30, there is a second upper snap-fit closure element 33 whose mating piece 34 is formed on the lower element 31". This can be readily seen in FIG. 1d. The second upper snap-fit closure element 33 is preferably formed by an upper and lower circumferential latch that hooks securely onto a connector piece protruding into the opening of the coupling part 2. Preferably, this connection between the upper and lower elements 3, 3" cannot be undone without being destroyed, so that, as can be seen in FIGS. 1e, 1f and 1g, the coupling part 2 and the breast cup attachment part 3 form one unit connected by the tamper-evident element 4.

Figure 1H:
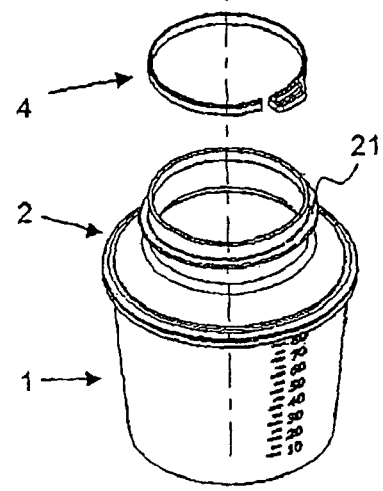
FIG. 1h shows a perspective representation of the breast cup set according to FIG. 1a after removal of the tamper-evident element.

If the tamper-evident element 4 is now removed, the entire breast cup attachment part 3, i.e. the upper and lower elements 3, 3", comes away from the coupling part 2, as can be seen in FIG. 1h. This separation means that, when the parts are joined again, it is not possible to obtain a sufficiently good connection any longer, so that this combination cannot be used again for pumping off milk.

Figure 1I:
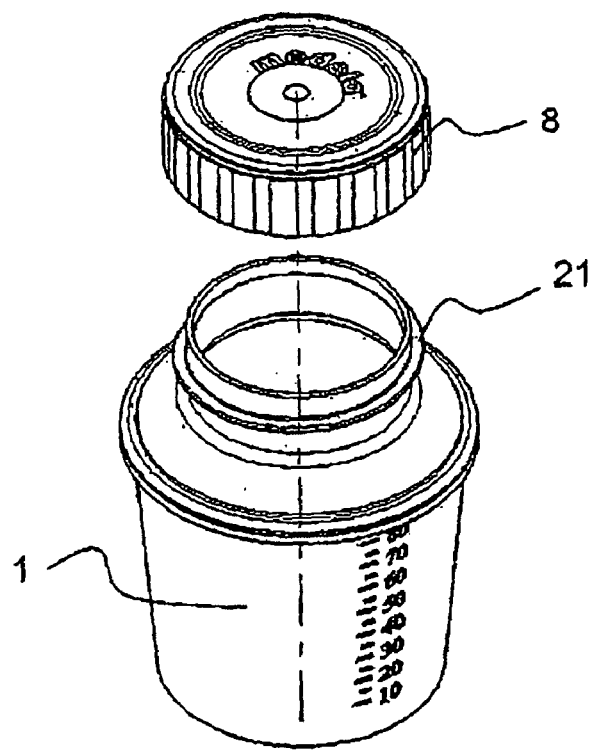
FIG. 1i shows the collection receptacle according to FIG. 1a with a closure lid, in an exploded view.
Figure 1K:
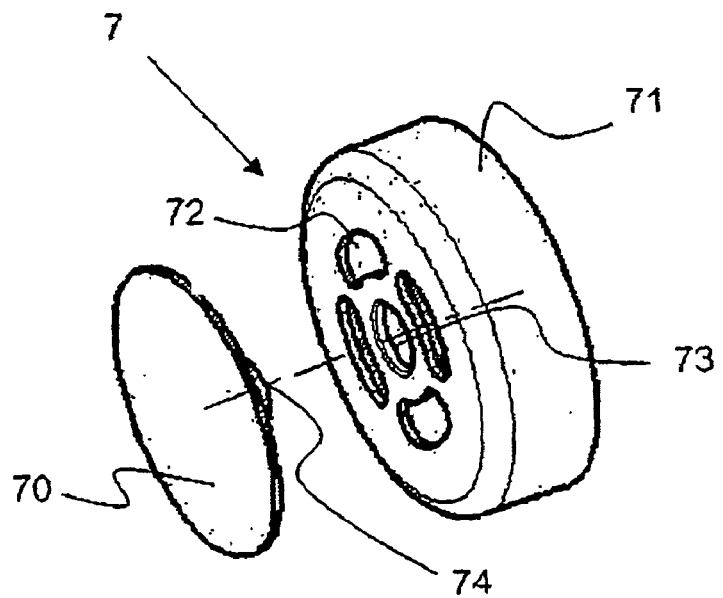

However, a beaker-shaped collection receptacle 1 is left together with an attached coupling part 2, and these together form a baby's bottle. The coupling part 2 forms a bottle neck. Since it is provided under the tamper-evident element 4 with an external thread 21, the bottle can be closed by a lid 8 until it is used. This is shown in FIG. 1i. At the time of use, the lid 8 can be removed, and a top with a teat can be applied in the known manner.

Figure 2A:
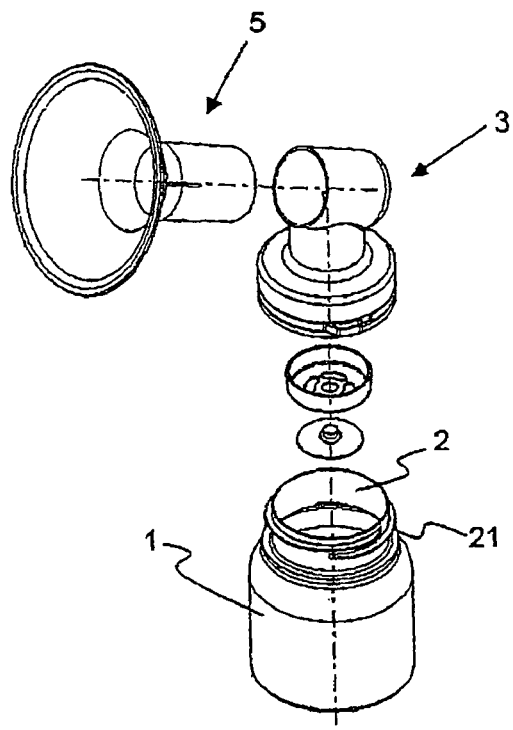
FIG. 2a shows a perspective representation of a breast cup set according to the invention in a second embodiment and in an exploded view.
Figure 2B:
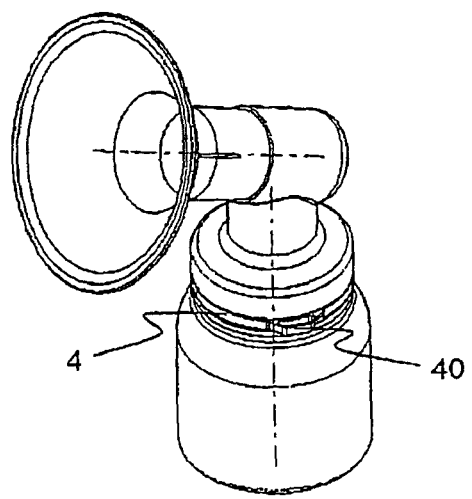
FIG. 2b shows the breast cup set according to FIG. 2a in the assembled state.
Figure 2C:
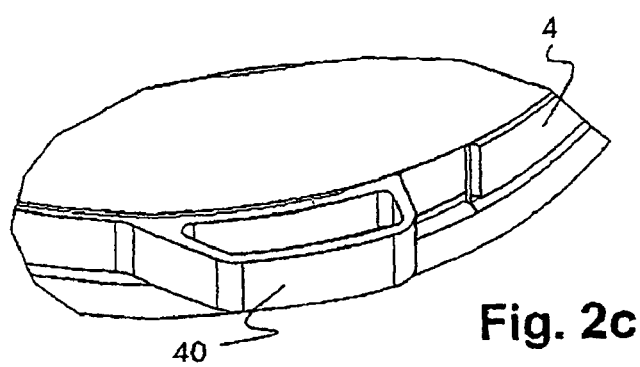
FIG. 2c shows an enlarged detail according to FIG. 2b.

In a second embodiment of the breast cup set according to the invention, shown in FIGS. 2a to 2c, the breast cup attachment part 3 is in one piece and the tamper-evident element 4 is formed integrally on it. Here once again, a snap-fit closure and a tamper-evident band ensure an irreversibly destructible connection with the coupling part 2. In this embodiment, the collection receptacle 1 and the coupling part 2 are formed by a one-piece bottle. In another variant, however, they are designed in two pieces according to FIG. 1b. In this example too, the breast cup funnel 5 can be pushed into the breast cup attachment part 3 at the time of use.

In the illustrative embodiment according to FIGS. 3a to 3c, the breast cup funnel 5 and the breast cup attachment part 3 are formed together in one piece. The tamper-evident element 4 is formed on the lower edge of the breast cup attachment part 3. In this example too, the collection receptacle 1 and the coupling part 2 can be formed by a one-piece bottle or they can form separate parts. In this example, the collection receptacle 1 does not have a round cross section, but a rectangular, in particular square cross section. This means it can be stored taking up less space than round bottles. Of course, the two-part bottles described above can also have such a rectangular or square shape.

Figure 4:
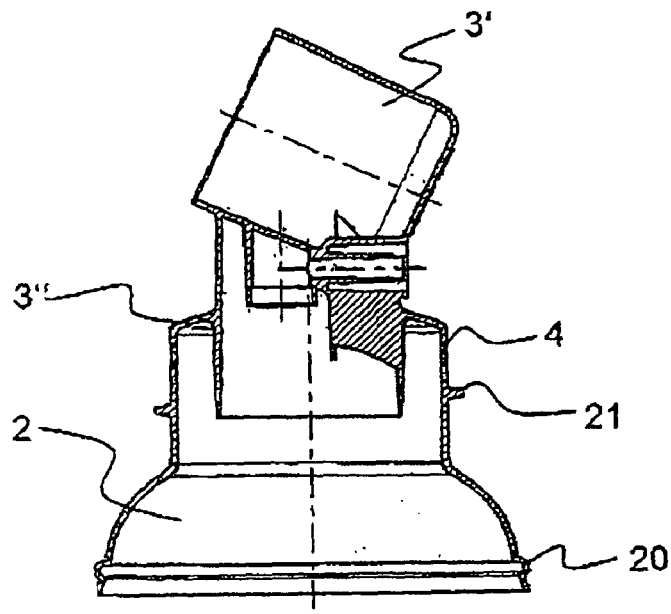
FIG. 4 shows a longitudinal section through an upper part of a breast cup set according to the invention in a fourth embodiment.

The embodiment according to FIG. 4 shows a breast cup attachment part and a coupling part connected integrally to one another. In this case too, the tamper-evident element is injection molded.

Figure 5A:
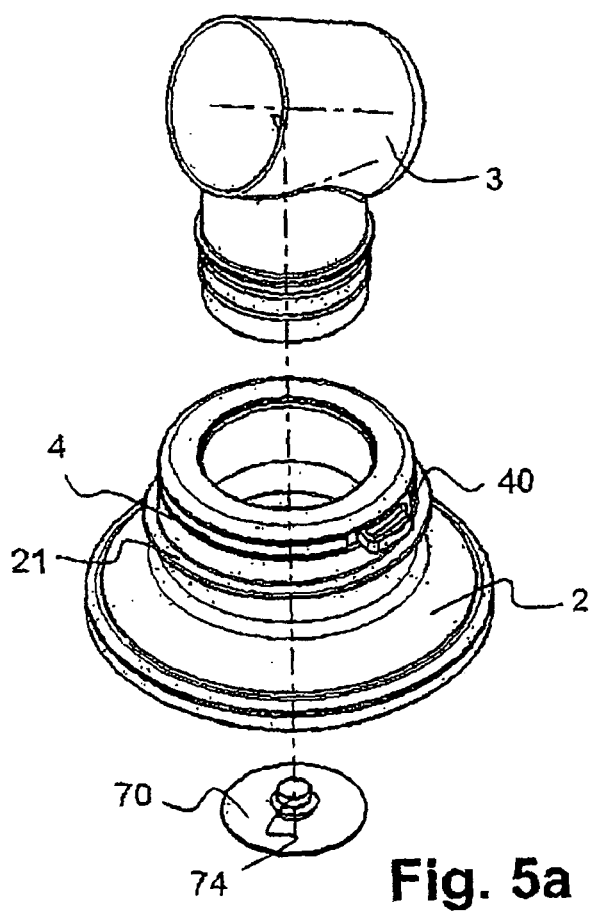
FIG. 5a shows a perspective representation of an upper part of a breast cup set according to the invention in a fifth embodiment and in an exploded view.
Figure 5B:
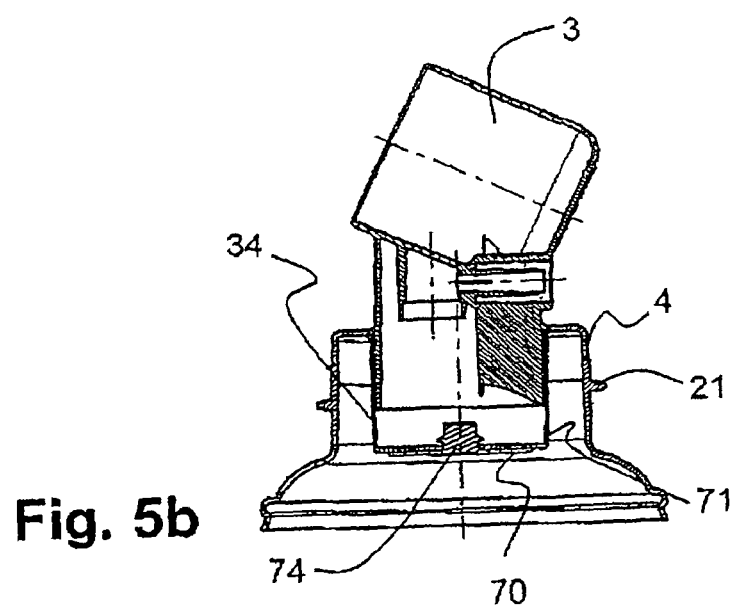

In the embodiment according to FIGS. 5a and 5b, the valve 7 is not arranged on the receptacle-side connector piece 30, but on a mating piece 34 protruding into the coupling part 2. The valve body 71 can be fitted onto or integrally formed on this mating piece 34.

The valve 7 can have a wide variety of shapes. In the embodiments described above, in particular in FIG. 1k, a valve 7 is disclosed which has a cylindrical valve body 71 and a membrane 70 covering this valve body 71. The valve body 71 is preferably made of a rigid material, in particular plastic. The membrane 70 is made of a flexible material, preferably rubber, caoutchouc or silicone or TPE.

The valve 7 is fixed in its position by the valve body 71 being pushed over a stub. On a front face, the valve body 71 has through-openings 72 and a centrally arranged receiver opening 73. Matching this, the membrane has a preferably centrally arranged connection button 74 which can be plugged into the receiver opening 73 in order to secure the membrane.

Figure 6:
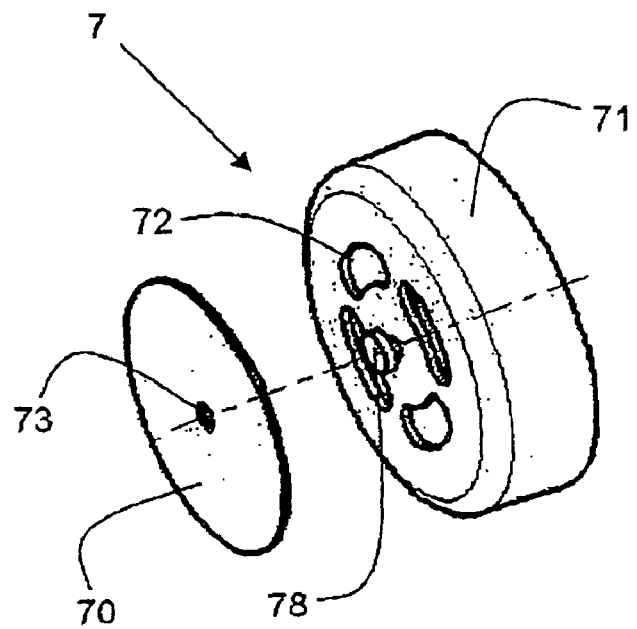
FIG. 6 shows a perspective representation of a valve according to a sixth embodiment.

However, other valves can also be used in the above-described embodiments of the breast cup set. Thus, as is shown in FIG. 6, a membrane receiver 78 in the form of a connection button can be arranged on the valve body 71, and the receiver opening 73 in the membrane 70.

Figure 7A:
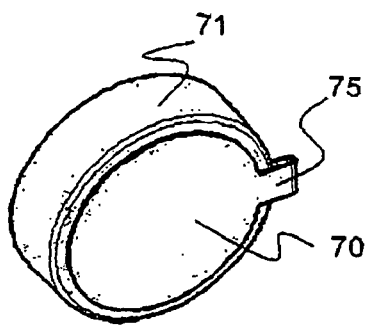
FIG. 7a shows a perspective representation of a valve according to a seventh embodiment from a first side.
Figure 7B:
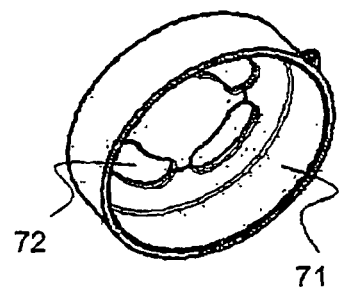
FIG. 7b shows a perspective representation of the valve according to FIG. 7a from a second side.
Figure 7C:
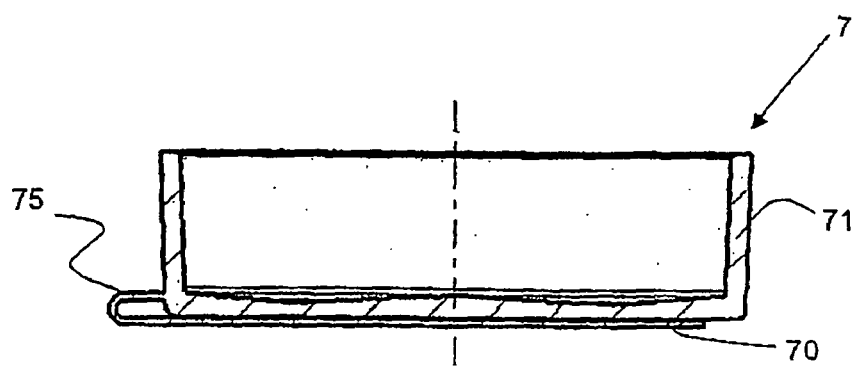

As is shown in FIGS. 7a to 7c, the membrane 70 can also be connected integrally to the valve body 71 via a hinge or a lip 75. In this case, the valve 7 is preferably made of a uniform material, the membrane having a thinner wall than the valve body.

Figure 8A:
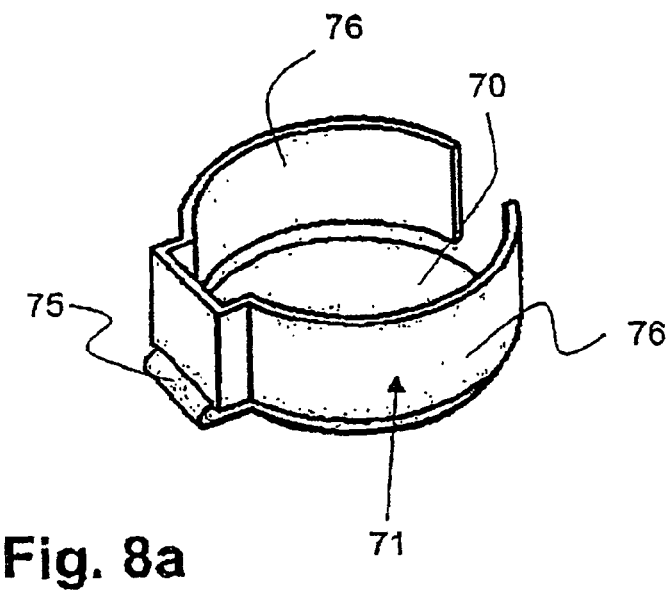
FIG. 8a shows a perspective representation of a valve according to an eighth embodiment.
Figure 8B:
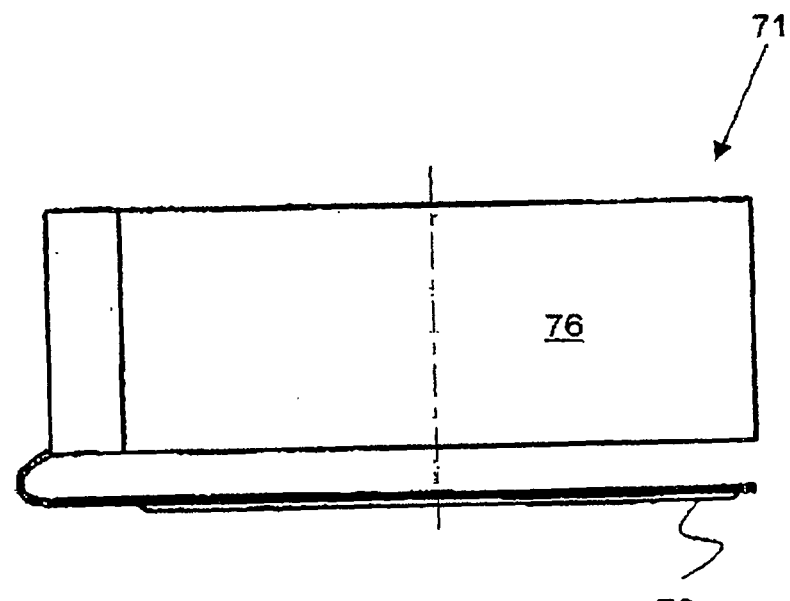

Moreover, the valve body 7 according to FIGS. 8a and 8b can be designed not with a closed jacket, but with a jacket that is open at one end. In this way, the two jacket parts 76 can be made resilient, which on the one hand makes it easier to fit the valve 7 in place and on the other hand improves its fit on the connector piece 30.

Figure 9A:
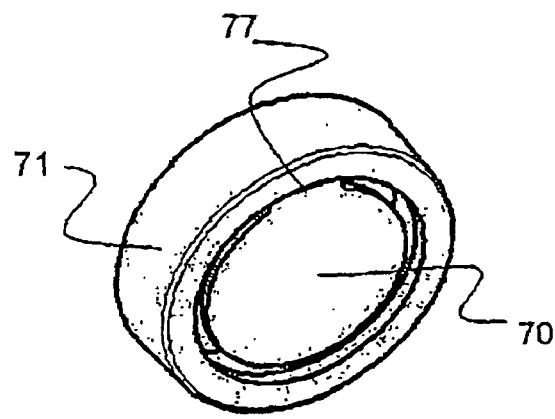
FIG. 9a shows a perspective representation of a valve according to a ninth embodiment, from a first side.
Figure 9B:
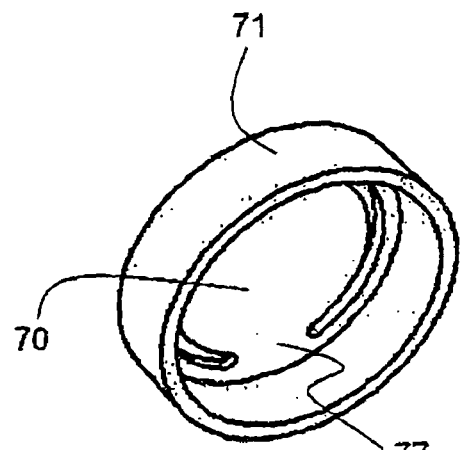
FIG. 9b shows a perspective representation of the valve according to FIG. 9a, from a second side.
Figure 9C:
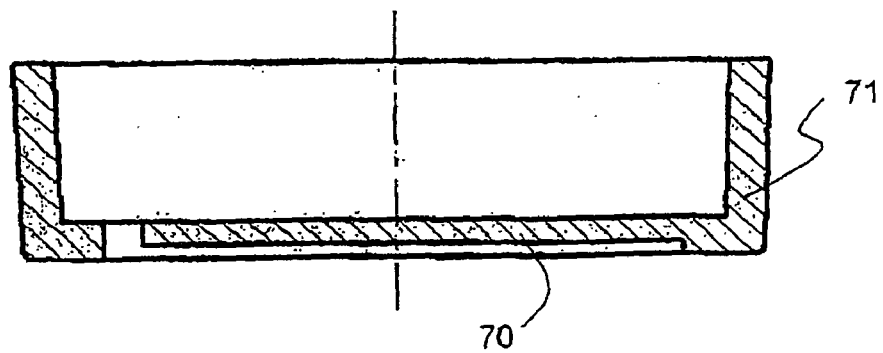

In another embodiment according to FIGS. 9a to 9c, the membrane 70 is integrally formed on the valve body 71 via a web 77, the two inner faces of the membrane and the inner faces of the valve body lying flush in one plane.

The breast cup set according to the invention can be produced inexpensively and, by virtue of its individual parts, can be provided in a sterile package that takes up little space. It additionally permits the use of the collection receptacle as a baby's bottle and yet ensures that it is impossible to reuse the set for pumping off breast milk.

The invention claimed is:

1. A disposable breast cup set, the set comprising

A coupling part for connection to a milk collection receptacle, a breast cup funnel, a milk collection receptacle, a breast cup attachment part for connection to the breast cup funnel, the breast cup attachment part being connected to the coupling part, wherein the coupling part and the breast cup attachment part are designed such, that separation of the coupling part and the breast cup attachment part for the first time is necessary in order to store or administer the milk collected in the collection receptacle, and wherein the breast cup set has a tamper-evident element connecting the breast cup attachment part and the coupling part to one another in such a way that the connection between the coupling part and the breast cup attachment part is destroyed irreversibly the first time the coupling part and the breast cup attachment part are separated or the first time the tamper-evident element is removed, thereby preventing the disposable breast cup set from reuse.

2. The breast cup set as claimed in claim 1, wherein the coupling part and breast cup attachment part can be separated from one another only when the tamper-evident element has been irreversibly destroyed.

3. The breast cup set as claimed in claim 1, wherein the milk collection receptacle is part of a bottle with a bottle neck, and wherein the tamper-evident element is a tear-open seal arranged on the bottle neck.

4. The breast cup set as claimed in claim 1, wherein the tamper-evident element is connected to the coupling part and/or to the breast cup attachment part via destructible webs.

5. The breast cup set as claimed in claim 1, wherein the tamper-evident element is a band extending around a partial or complete circumference of the coupling part.

6. The breast cup set as claimed in claim 1, wherein the set comprises a milk collection receptacle that is formed in one piece with the coupling part.

7. The breast cup set as claimed claim 1, wherein the set comprises a milk collection receptacle which is beaker-shaped, can be connected to the coupling part, and forms a closable bottle together with the coupling part.

8. The breast cup set as claimed in claim 7, wherein the coupling part and collection receptacle can be connected to one another via a snap-fit closure.

9. The breast cup set as claimed in claim 1, wherein the coupling part is provided with an external thread.

10. The breast cup set as claimed in claim 9, wherein the tamper-evident element is arranged above the external thread.

11. The breast cup set as claimed in claim 1, wherein the breast cup attachment part has an upper element and a lower element, the upper element being able to be plugged into the lower element and being able to be fixed by means of a snap-fit closure.

12. The breast cup set as claimed in claim 11, wherein the lower element is connected to the coupling part by means of the tamper-evident element.

13. The breast cup set as claimed in claim 10, further comprising a disposable valve which closes a receptacle-side inlet opening of the breast cup attachment part, the disposable valve having a valve body provided with through-openings, and a valve membrane that closes these through-openings, and wherein the valve body is arranged on an inwardly protruding mating piece of the lower element.

14. The breast cup set as claimed in claim 1, further comprising a disposable valve which closes a receptacle-side inlet opening of the breast cup attachment part, the disposable valve having a valve body provided with through-openings, and a valve membrane that closes these through-openings, and wherein the valve membrane is formed integrally on the valve body.

15. A disposable breast pumping kit comprising:
 a coupling part for connection to a milk receptacle;
 a breast cup attachment part including a breast funnel, the coupling part and the breast cup attachment part being connected to one another;
 a tube connected to the breast cup attachment part for connection to a vacuum source; and
 a mechanism that prevents the disposable breast pumping kit from being re-used.

16. The disposable breast pumping kit of claim 15 wherein the mechanism prevents the disposable breast pumping kit from being re-used by disabling a vacuum functionality of the disposable breast pumping kit.

17. The disposable breast pumping kit of claim 15 wherein the vacuum source comprises a breast pump.

* * * * *